(12) United States Patent
Peterson et al.

(10) Patent No.: US 9,707,408 B2
(45) Date of Patent: Jul. 18, 2017

(54) EMERGENCY MONITOR-DEFIBRILLATOR WITH TELEMEDICINE CAPABILITY AND REMOTE ACTIVATION

(71) Applicant: Physio-Control, Inc., Redmond, WA (US)

(72) Inventors: Kenneth J. Peterson, Bellevue, WA (US); Dana S. Lewis, Woodinville, WA (US); Mitchell A. Smith, Sammamish, WA (US); Cheryl Protas, Redmond, WA (US); David B. Stewart, Carnation, WA (US); Gregory T. Kavounas, Bellevue, WA (US)

(73) Assignee: PHYSIO-CONTROL, INC., Redmond, WA (US)

( * ) Notice: Subject to any disclaimer, the term of this patent is extended or adjusted under 35 U.S.C. 154(b) by 0 days.

(21) Appl. No.: 15/154,897

(22) Filed: May 13, 2016

(65) Prior Publication Data

US 2016/0256700 A1  Sep. 8, 2016

Related U.S. Application Data

(62) Division of application No. 14/718,403, filed on May 21, 2015, now Pat. No. 9,364,682.

(Continued)

(51) Int. Cl.
*A61N 1/00* (2006.01)
*A61N 1/39* (2006.01)
(Continued)

(52) U.S. Cl.
CPC .......... *A61N 1/3993* (2013.01); *A61N 1/046* (2013.01); *A61N 1/3925* (2013.01); *A61N 1/3987* (2013.01); *G06F 19/3406* (2013.01); *G06F 19/3418* (2013.01); *G08B 21/02* (2013.01); *G08B 5/36* (2013.01)

(58) Field of Classification Search
CPC .... A61N 1/046; A61N 1/3925; A61N 1/3987; A61N 1/3993; G06F 19/3406; G06F 19/3418; G08B 21/02; G08B 5/36
See application file for complete search history.

(56) References Cited

U.S. PATENT DOCUMENTS 5,489,293 A  *  2/1996  Pless .................... A61N 1/3956
                                                 607/5
6,409,660 B1     6/2002  Sjoqvist
(Continued)

*Primary Examiner* — George Manuel
(74) *Attorney, Agent, or Firm* — Kavounas Patent Law Office, PLLC

(57) ABSTRACT

In embodiments, an emergency external defibrillator system is configured for use by a local rescuer in cooperation with a remote rescuer to assist a patient. The external defibrillator system includes a sensor to generate a patient value that represents a physiological parameter of the patient. The system also includes a communication module to transmit the patient value to another device of a remote rescuer, and to receive in response an incoming message that contains an encoded discharge instruction. The system also includes a processor that can decode the discharge instruction, and cause the system to defibrillate or pace the patient. An advantage is that therapy can be initiated remotely from the remote rescuer, who may be better trained, more confident, and less under the stress of the moment than the local rescuer.

21 Claims, 9 Drawing Sheets

*DEFIBRILLATION SCENE*

Related U.S. Application Data

(60) Provisional application No. 62/007,367, filed on Jun. 3, 2014.

(51) Int. Cl.
*G08B 21/02* (2006.01)
*G06F 19/00* (2011.01)
*A61N 1/04* (2006.01)
*G08B 5/36* (2006.01)

(56) References Cited

U.S. PATENT DOCUMENTS

| | | | |
|---|---|---|---|
| 7,383,088 B2 * | 6/2008 | Spinelli | A61N 1/37282 607/30 |
| 2009/0035740 A1 | 2/2009 | Reed et al. | |
| 2010/0324612 A1 | 12/2010 | Matos | |
| 2011/0178373 A1 | 7/2011 | Pacey et al. | |
| 2013/0154851 A1 | 6/2013 | Gaskill et al. | |
| 2015/0116126 A1 | 4/2015 | Hyde et al. | |
| 2015/0119652 A1 | 4/2015 | Hyde et al. | |

* cited by examiner

*DEFIBRILLATION SCENE*

| TYPE OF EXTERNAL DEFIBRILLATOR SYSTEM | INTENDED TO BE USED BY PERSONS: | |
|---|---|---|
| | IN THE MEDICAL PROFESSIONS | NOT IN THE MEDICAL PROFESSIONS |
| DEFIBRILLATOR – MONITOR | √ | |
| AED | √ | √ |

FIG. 2 *TWO MAIN TYPES OF EXTERNAL DEFIBRILLATOR SYSTEMS*

COMPONENTS OF EXTERNAL DEFIBRILLATOR SYSTEM

*COMPONENTS OF EXTERNAL DEFIBRILLATOR SYSTEM*

FIG. 8      *METHODS*

*COMPONENTS OF EXTERNAL DEFIBRILLATOR SYSTEM*

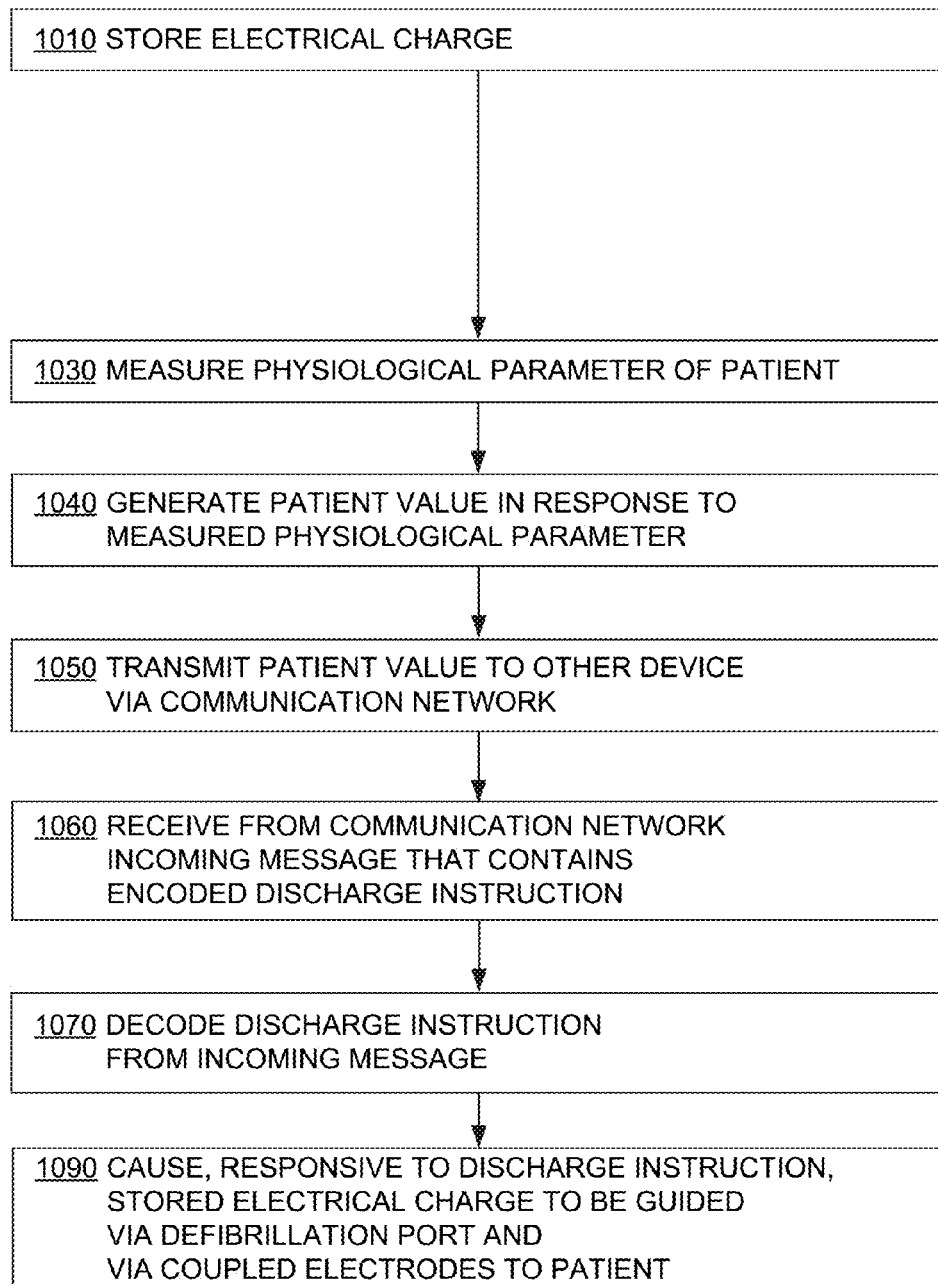
FIG. 10    *METHODS*

EMERGENCY MONITOR-DEFIBRILLATOR WITH TELEMEDICINE CAPABILITY AND REMOTE ACTIVATION

CROSS REFERENCE TO RELATED PATENT APPLICATIONS

This patent application is a divisional of U.S. patent application Ser. No. 14/718,403, filed on May 21, 2015, which in turn claims priority from U.S. Provisional Patent Application Ser. No. 62/007,367, filed on Jun. 3, 2014, the disclosure of which is hereby incorporated by reference.

BACKGROUND

In humans, the heart beats to sustain life. In normal operation, it pumps blood through the various parts of the body, thanks to its electrical control system. More particularly, the sinoatrial (SA) node generates an electrical impulse, which generates further electrical signals. These further signals cause the various heart chambers to contract in the correct sequence. The electrical pattern created by the sinoatrial (SA) node is called a sinus rhythm.

Sometimes, however, the electrical control system of the heart malfunctions, which can cause the heart to beat irregularly, or not at all. The cardiac rhythm is then generally called an arrhythmia. Arrhythmias may be caused by electrical activity from locations in the heart other than the SA node. Some types of arrhythmia may result in inadequate blood flow, thus reducing the amount of blood pumped to the various parts of the body. Some arrhythmias may even result in a Sudden Cardiac Arrest (SCA). In a SCA, the heart fails to pump blood effectively, and, if not treated, death can occur. In fact, it is estimated that SCA results in more than 250,000 deaths per year in the United States alone. Further, a SCA may result from a condition other than an arrhythmia.

One type of arrhythmia associated with SCA is known as Ventricular Fibrillation (VF). VF is a type of malfunction where the ventricles make rapid, uncoordinated movements, instead of the normal contractions. When that happens, the heart does not pump enough blood to deliver enough oxygen to the vital organs. The person's condition will deteriorate rapidly and, if not reversed in time, they will die soon, e.g. within ten minutes. A present or prior VF episode is when a person typically starts becoming characterized as a patient in these contexts.

Ventricular Fibrillation can often be reversed using a life-saving device called a defibrillator. A defibrillator, if applied properly, can administer an electrical shock to the heart. The shock may terminate the VF, thus giving the heart the opportunity to resume pumping blood. If VF is not terminated, the shock may be repeated, often at escalating energies.

A challenge with defibrillation is that the electrical shock must be administered very soon after the onset of VF. There is not much time: the survival rate of patients suffering from VF decreases by about 10% for each minute the administration of a defibrillation shock is delayed. After about 10 minutes, the rate of survival for SCA victims averages less than 2%.

VF can occur unpredictably, even to a patient who is not considered at risk. When VF occurs, the patient collapses, because blood flow has stopped. They should receive therapy quickly. A different type of defibrillator can be used, which is called an external defibrillator. External defibrillators have been made portable, so they can be brought to a potential VF victim quickly enough to revive them.

A situation of a VF is unpredictable, unexpected, and fraught with danger for the victim. Even a trained rescuer may perform less optimally, under the intensity of the moment.

BRIEF SUMMARY

The present description gives instances of devices, systems, storage media that store programs, and methods, the use of which may help overcome problems and limitations of the prior art.

In embodiments, an emergency external defibrillator system is configured for use by a local rescuer in cooperation with a remote rescuer, to assist a patient. The external defibrillator system includes a sensor to generate a patient value that represents a physiological parameter of the patient. The system also includes a communication module to transmit the patient value to another device of a remote rescuer, and to receive in response an incoming message that contains an encoded sound. For the local rescuer, the system also includes a screen to display the patient value, and a speaker to play the sound concurrently with the screen displaying the patient value. An advantage is that the local rescuer can receive guidance from the remote rescuer.

In embodiments, an emergency external defibrillator system is configured for use by a local rescuer in cooperation with a remote rescuer to assist a patient, and for remote activation by the remote rescuer. The external defibrillator system includes a sensor to generate a patient value that represents a physiological parameter of the patient. The system also includes a communication module to transmit the patient value to another device of a remote rescuer, and to receive in response an incoming message that contains an encoded discharge instruction. The system also includes a processor that can decode the discharge instruction, and cause the system to defibrillate or pace the patient. An advantage is that therapy can be initiated remotely from the remote rescuer, who may be better trained, more confident, and less under the stress of the moment than the local rescuer.

These and other features and advantages of this description will become more readily apparent from the Detailed Description, which proceeds with reference to the associated drawings in which:

BRIEF DESCRIPTION OF THE DRAWINGS

FIG. 2 is a table listing two main types of the external defibrillator system shown in FIG. 1, and who they might be used by.

FIG. 10 is a flowchart for illustrating methods according to embodiments.

DETAILED DESCRIPTION

As has been mentioned, the present description is about devices, systems, storage media that store programs, and methods. Embodiments are now described in more detail.

Figure 1:
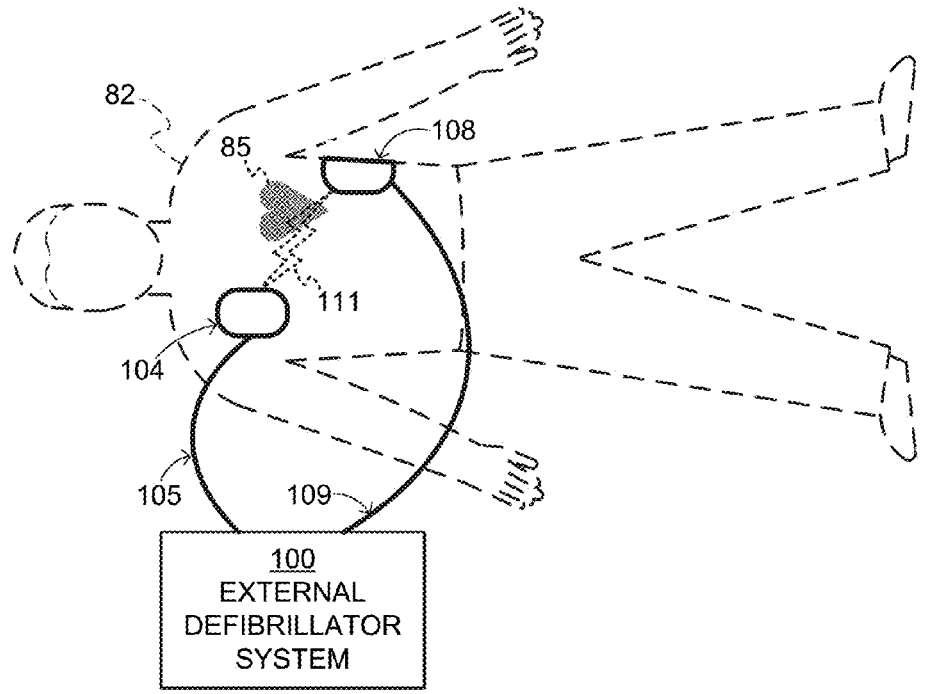
FIG. 1 is a diagram of a scene where an external defibrillator system is used to save the life of a patient according to embodiments.

FIG. 1 is a diagram of a defibrillation scene. A patient 82 is lying on his back. Patient 82 could be a patient in a hospital, or a pre-hospital patient such as someone found initially unconscious. Patient 82 is experiencing a condition in their heart 85, which could be Ventricular Fibrillation (VF). VF can be preceded by Ventricular Tachycardia (VT).

A portable external defibrillator system 100 has been brought close to patient 82. At least two defibrillation electrodes 104, 108 are usually provided with external defibrillator system 100, and are sometimes called electrodes 104, 108. Electrodes 104, 108 are coupled with external defibrillator system 100 via respective electrode leads 105, 109. A rescuer (not shown) has attached electrodes 104, 108 to the skin of patient 82. Defibrillator system 100 is administering, via electrodes 104, 108, a brief, strong electric pulse 111 through the body of patient 82. Pulse 111, also known as a defibrillation shock, goes also through heart 85, in an attempt to restart it, for saving the life of patient 82.

Defibrillator system 100 can be one of different types, each with different sets of features and capabilities. The set of capabilities of defibrillator system 100 is determined by planning who would use it, and what training they would be likely to have. Examples are now described.

FIG. 2 is a table listing two main types of external defibrillators, and who they are primarily intended to be used by. A first type of defibrillator system 100 is generally called a defibrillator-monitor, because it is typically formed as a single unit in combination with a patient monitor. A defibrillator-monitor is sometimes called monitor-defibrillator. A defibrillator-monitor is intended to be used by persons in the medical professions, such as doctors, nurses, paramedics, emergency medical technicians, etc. Such a defibrillator-monitor is intended to be used in a pre-hospital or hospital scenario.

As a defibrillator, the device can be one of different varieties, or even versatile enough to be able to switch among different modes that individually correspond to the varieties. One variety is that of an automated defibrillator, which can determine whether a shock is needed and, if so, charge to a predetermined energy level and instruct the user to administer the shock. Another variety is that of a manual defibrillator, where the user determines the need and controls administering the shock.

As a patient monitor, the device has features additional to what is minimally needed for mere operation as a defibrillator. These features can be for monitoring physiological indicators of a patient in an emergency scenario. These physiological indicators are also called physiological parameters, and are typically monitored as signals. For example, these physiological parameters can include a patient's full ECG (electrocardiogram) signals, or impedance between two electrodes. Additionally, these physiological parameters can be, according to embodiments, the physiological parameter can be one of the patient's peripheral capillary oxygen saturation/pulse oximetry (SpO2), carboxyhemoglobin, methemoglobin (SpMet), a concentration or partial pressure of carbon dioxide in the respiratory gases that is also known as capnography and end-tidal carbon dioxide (EtCO2), Non-Invasive Blood Pressure (NIBP), tissue oxygen saturation (StO2), temperature, a regional oxygen saturation index (Rs-O2), and an invasive pressure. These physiological parameters can be further stored and/or transmitted as patient data.

The patient's peripheral capillary oxygen saturation (SpO2), is an estimation of the oxygen saturation level. Oxygen saturation is a term referring to the concentration of oxygen in the blood. It measures the percentage of hemoglobin binding sites in the bloodstream occupied by oxygen.

Carboxyhemoglobin is a measurement that allows clinicians to noninvasively and quickly detect elevated levels of carbon monoxide in the blood-facilitating earlier diagnosis and treatment, for patients poisoned by carbon monoxide.

Tissue oxygen saturation can include measuring hemoglobin oxygen saturation in the microcirculation, where oxygen diffuses to tissue cells. In some embodiments, measuring tissue oxygen saturation permits real-time, continuous monitoring of peripheral perfusion.

A second type of external defibrillator system 100 is generally called an AED, which stands for "Automated External Defibrillator". An AED typically makes the shock/no shock determination by itself, automatically. Indeed, it can sense enough physiological conditions of the patient 82 via only the shown defibrillation electrodes 104, 108 of FIG. 1. In its present embodiments, an AED can either administer the shock automatically, or instruct the user to do so, e.g. by pushing a button. Being of a much simpler construction, an AED typically costs much less than a defibrillator-monitor. As such, it makes sense for a hospital, for example, to deploy AEDs at its various floors, in case the more expensive defibrillator-monitor is more critically being deployed at an Intensive Care Unit, and so on.

AEDs, however, can also be used by people who are not in the medical professions. More particularly, an AED can be used by many professional first responders, such as policemen, firemen, etc. Even a person with first-aid and CPR/AED training can use one. And AEDs increasingly can supply instructions to whoever is using them.

AEDs are thus particularly useful, because it is so critical to respond quickly, when a patient suffers from VF. Indeed, the people who will first reach the VF sufferer may not be in the medical professions.

Increasing awareness has resulted in AEDs being deployed in public or semi-public spaces, so that even a member of the public can use one, if they have obtained first aid and CPR/AED training on their own initiative. This way, defibrillation can be administered soon enough after the onset of VF, to hopefully be effective in rescuing the patient.

There are additional types of external defibrillators, which are not listed in FIG. 2. For example, a hybrid defibrillator can have aspects of an AED, and also of a defibrillator-monitor. A usual such aspect is additional ECG monitoring capability.

Figure 3:
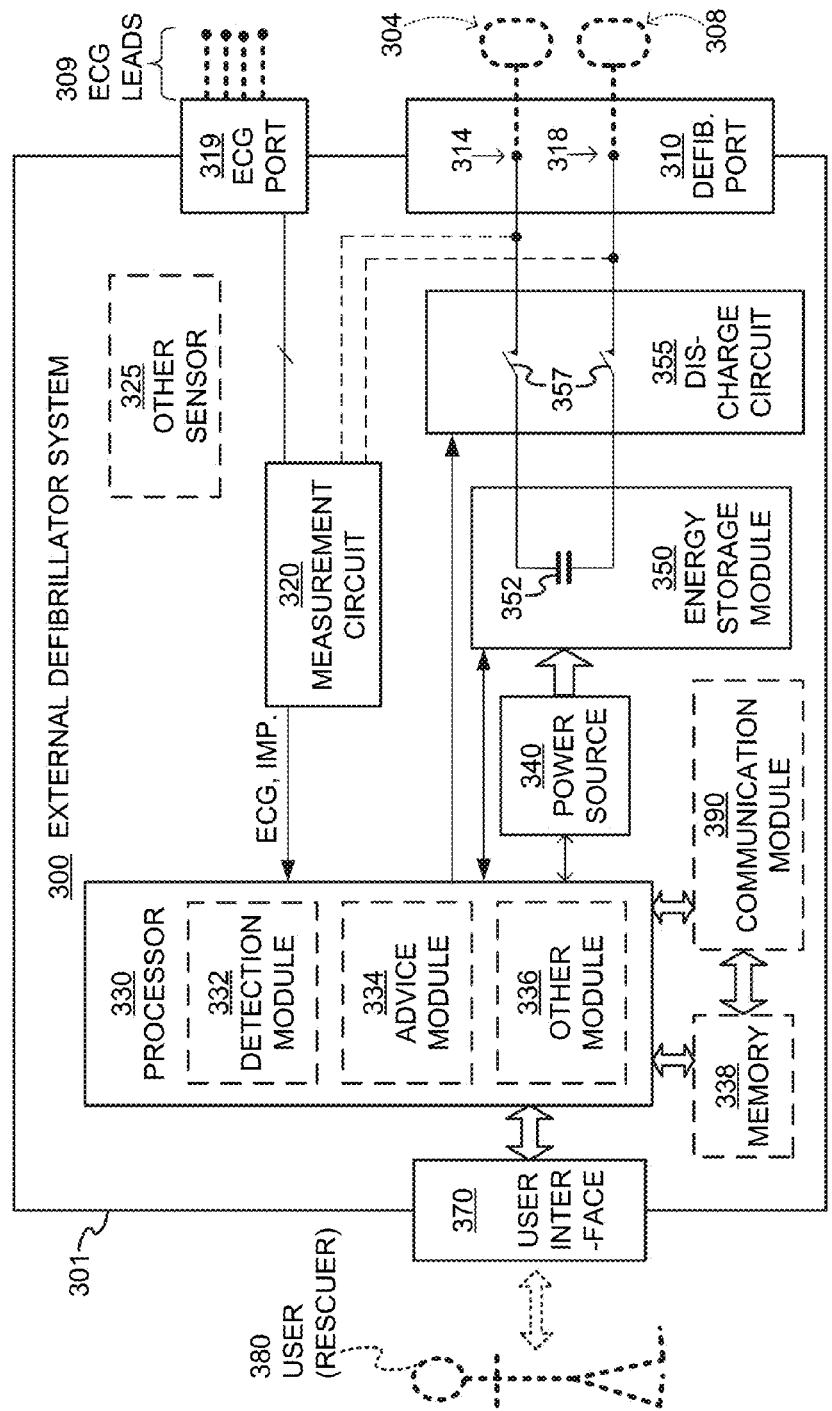
FIG. 3 is a diagram showing components of a sample external defibrillator system, such as the one shown in FIG. 1, which is made according to embodiments.

FIG. 3 is a diagram showing components of an external defibrillator system 300 made according to embodiments. These components can be, for example, in external defibrillator system 100 of FIG. 1. These components of FIG. 3 can be provided in a housing 301, which is also known as casing 301. One or more of them can be provided in an Application Specific Integrated Circuit ("ASIC").

External defibrillator system 300 is intended for use by a user 380, who would be the rescuer. Defibrillator system 300 typically includes a defibrillation port 310, such as a socket in housing 301. Defibrillation port 310 includes nodes 314, 318. Defibrillation port 310 can be configured such that defibrillation electrodes 304, 308, which can be similar to electrodes 104, 108, can be electrically coupled to defibrillation port 310. For example, defibrillation electrodes 304, 308 can be plugged into defibrillation port 310 so as to make electrical contact with nodes 314, 318, respectively. It is also possible that electrodes can be connected continuously to defibrillation port 310, etc. Either way, defibrillation port 310 can be configured such that an electrical charge that has been stored in defibrillator system 300 can be guided through defibrillation port 310 via electrodes 304, 308 to the patient (not shown in FIG. 3). The electrical charge may have been stored in defibrillator system 300 as will be seen later in this document.

If defibrillator system 300 is actually a defibrillator-monitor, as was described with reference to FIG. 2, then it will typically also have an ECG port 319 in housing 301, for plugging in ECG leads 309. ECG leads 309 can help sense an ECG signal, e.g. a 12-lead signal, or from a different number of leads. Moreover, a defibrillator-monitor could have additional ports (not shown).

Additionally, a defibrillator system according to embodiments could have a sensor. The sensor can be configured to measure a physiological parameter of a patient, and to generate a patient value in response to the measured physiological parameter. The sensor can be measurement circuit 320 that is described below, in which case the patient value is a value of an ECG signal or an impedance signal. Or, the sensor can be another sensor 325, which may have any number of implementations as being the appropriate sensor for measuring a number of possible physiological parameters mentioned above.

Defibrillator system 300 also includes a measurement circuit 320. Measurement circuit 320 receives physiological signals from ECG port 319, and also from other ports, if provided. These physiological signals are sensed, and information about them is rendered by circuit 320 as data, or other signals, etc.

If defibrillator system 300 is actually an AED, it may lack ECG port 319. Measurement circuit 320 can obtain physiological signals through nodes 314, 318 instead, when defibrillation electrodes 304, 308 are attached to patient 82. In these cases, a patient's ECG signal can be sensed as a voltage difference between electrodes 304, 308. Plus, impedance between electrodes 304, 308 can be sensed for detecting, among other things, whether electrodes 304, 308 have been inadvertently disconnected from the patient.

Defibrillator system 300 also includes a processor 330. Processor 330 may be implemented in a number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 330 can be considered to have a number of modules. One such module can be a detection module 332, which senses outputs of measurement circuit 320. Detection module 332 can include a VF detector, a VT detector, and so on. Thus, the patient's sensed ECG can be used to determine whether the patient is experiencing VF or VT.

Another such module in processor 330 can be an advice module 334, which arrives at advice based on outputs of detection module 332. Advice module 334 can include a Shock Advisory Algorithm, implement decision rules, and so on. The advice can be to shock, to not shock, to administer other forms of therapy, and so on. If the advice is to shock, some external defibrillator embodiments merely report that to the user, and prompt them to do it. Other embodiments further execute the advice, by administering the shock. Shocking is by delivering a stored electrical charge, which is also known as discharging. If the advice is to administer CPR, defibrillator system 300 may further issue prompts for it, and so on.

Processor 330 can include additional modules, such as module 336, for other functions. In addition, other sensor 325 may be operated in part by processor 330, etc.

Defibrillator system 300 optionally further includes a memory 338, which can work together with processor 330. Memory 338 may be implemented in any number of ways. Such ways include, by way of example and not of limitation, nonvolatile memories (NVM), read-only memories (ROM), random access memories (RAM), any combination of these, and so on. Memory 338, if provided, can include programs for processor 330, and so on. The programs can be operational for the inherent needs of processor 330, and can also include protocols and ways that decisions can be made by advice module 334. In addition, memory 338 can store prompts for user 380, etc. Moreover, memory 338 can store patient data.

Defibrillator system 300 may also include a power source 340. To enable portability of defibrillator system 300, power source 340 typically includes a battery. Such a battery is typically implemented as a battery pack, which can be rechargeable or not. Sometimes, a combination is used, of rechargeable and non-rechargeable battery packs. Other embodiments of power source 340 can include AC power override, for where AC power will be available, and so on. In some embodiments, power source 340 is controlled by processor 330.

Defibrillator system 300 additionally includes an energy storage module 350. Module 350 can be configured to store electrical energy in the form of an electrical charge, when preparing it for sudden discharge to administer a shock. Module 350 can be charged from power source 340 to the right amount of energy, as controlled by processor 330. In typical implementations, module 350 includes one or more capacitors 352, and so on.

Defibrillator system 300 moreover includes a discharge circuit 355. Circuit 355 can be controlled to permit the energy stored in module 350 to be discharged to nodes 314, 318, and thus also to defibrillation electrodes 304, 308. Circuit 355 can include one or more switches 357. Switches 357 can be made in a number of ways, such as by an H-bridge, and so on.

Defibrillator system 300 further includes a user interface 370 for user 380. User interface 370 can be made in any number of ways. For example, interface 370 may include output devices, which can be visual, audible or tactile, for communicating to a user. An output device can be configured to output a warning, which warns or instructs the patient or a bystander to do something. An output device can be a light or a screen to display what is detected and measured, and provide visual feedback to the rescuer for their resuscitation attempts, and so on. Interface 370 may also include a speaker, to issue voice prompts, etc. Sounds, images, vibrations, and anything that can be perceived by a human can also be called human perceptible indications. Interface 370 may additionally include input devices for receiving inputs from users. Such input devices may include various controls, such as pushbuttons, keyboards, touch-screens, a microphone, and so on. In addition, discharge circuit 355 can be controlled by processor 330, or directly by user 380 via user interface 370, and so on.

Defibrillator system 300 can optionally include other components. For example, a communication module 390 may be provided for communicating with other machines. Such communication can be performed wirelessly, or via wire, or by infrared communication, and so on. This way, data can be communicated, such as patient data, incident information, therapy attempted, CPR performance, and so on. Communication module 390, like other modules and units in embodiments may be implemented by a single module, multiple modules, etc.

Figure 4:
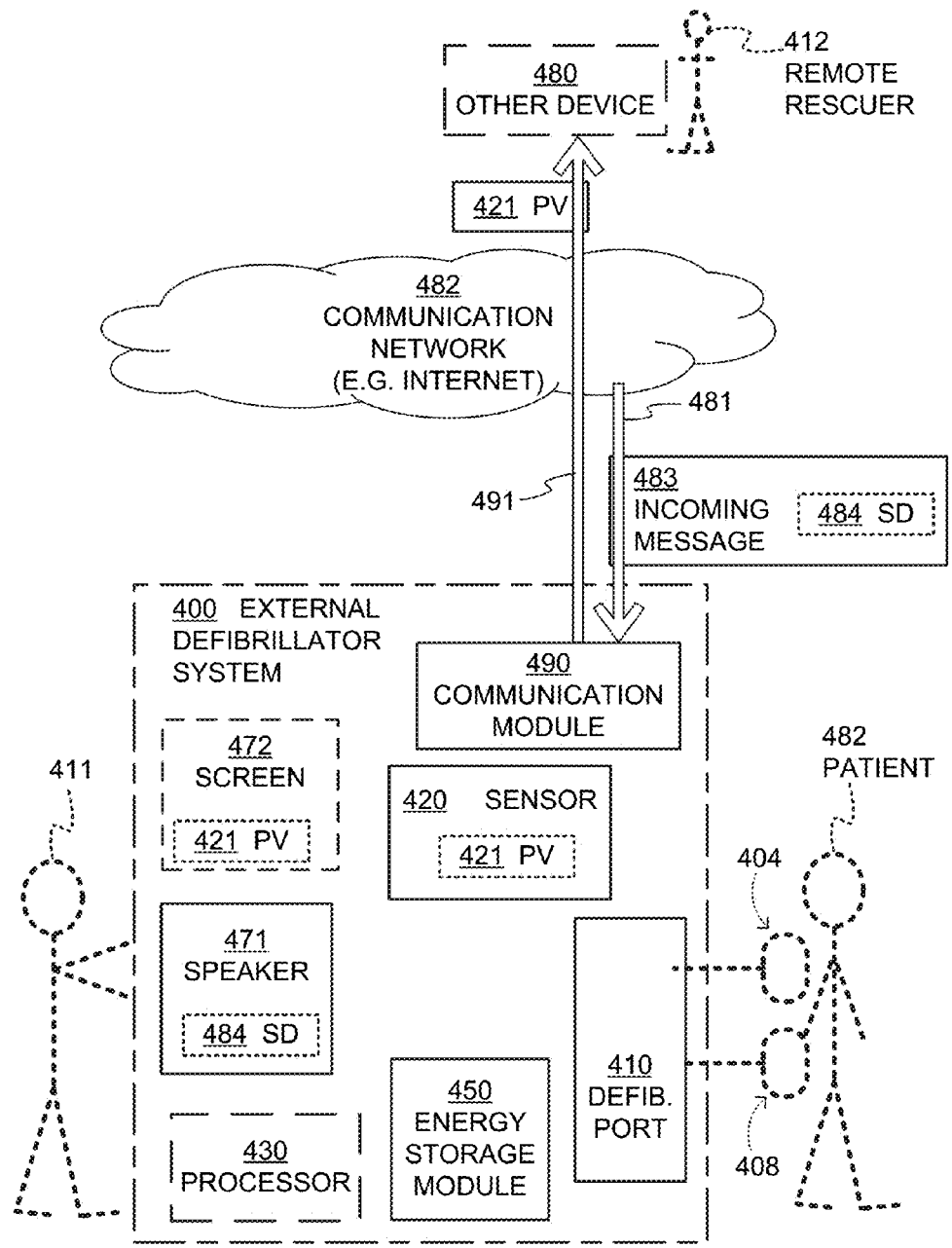
FIG. 4 is a diagram showing sample components of an external defibrillator system that is made and operates according to embodiments.

FIG. 4 is a diagram showing sample components of an external defibrillator system 400 that is made according to embodiments. External defibrillator system 400 can be a monitor-defibrillator that is used to respond to emergency patients in both the Hospital and Pre-Hospital Environments. System 400 can be configured for use by a local rescuer 411 in cooperation with a remote rescuer 412 to assist a patient 482. Local rescuer 411 is typically a trained first responder, such as a paramedic, etc. Local rescuer 411 could also be a bystander. Remote rescuer 412 can be a doctor or other trained attendant who is advising in this situation.

System 400 may be provided as a single device and maybe in a single housing. In some embodiments, some components, such as sensor 420, can be separable from the remainder of the single device. System 400 can assist patient 482 with the help of electrodes 404, 408, which can be applied by local rescuer 411. For example, local rescuer 411 can be capable of carrying external defibrillator system 400, and of attaching electrodes 404, 408 to patient 482.

System 400 includes an energy storage module 450 that can be as energy storage module 350, a defibrillation port 410 that can be as defibrillation port 310, and a sensor 420 that can be as measurement circuit 320 or other sensor 325. Sensor 420 can be configured to measure a physiological parameter of patient 482, and to generate a patient value PV 421 in response to the measured physiological parameter, as described in more detail above.

System 400 also includes a screen 472. Screen 472 can be part of a broader user interface for the use of local rescuer 411. This broader user interface may also include a speaker 471, another screen, etc. Screen 472 can be configured to display patient value PV 421 to local rescuer 411. This broader user interface may be used by local rescuer 411 to operate system 400, and also possibly to communicate with remote rescuer 412.

System 400 also includes a communication module 490, which can be as was described for communication module 390. Communication module 490 can be configured to stream real-time patient information, which may include vital sign measurements, vital sign waveforms, and treatment event information (drugs administered, shocks administered, pacing administered, results of advanced diagnostic algorithms, video from advanced diagnostic tools such as video laryngoscope and ultrasound, location information, patient demographics, etc. In addition, communication module 490 may facilitate audio and video channels to provide visual information of patient 482 and contextual information from the scene.

In particular, communication module 490 can be configured to transmit patient value PV 421 to another device 480 via a communication network 482 that can be the internet. This transmission is indicated in FIG. 4 with arrow 491, and can be through wireless or even wired connections. A variety of wireless communication methods can be used to communicate from communication module 490 to the cloud, including but not limited to Bluetooth, ZigBee, Wi-Fi, and all versions of Cellular (3G, 4G, LTE, GSM, GPRS, CDMA, etc.). A memory (not shown) may indicate an address of other device 480 in network 482. From the point of view of system 400, other device 480 and remote rescuer 412 are in the cloud. Access security can be provided at the receiving ends, to ensure that data is available only to authorized users.

Other device 480 can be a computer system, a smartphone, a tablet, etc., and can be used by remote rescuer 412. Only one remote rescuer 412 is shown, although there can be a number of them, and they could be communicating with each other, plus with any destination care center. All such participating remote rescuers could be contributing data, diagnosis, advice and consults, alerts, and patient receipt readiness operations. For example, a manager of the overall health care provider system (e.g. Medical Director of an Emergency Medical System) can actively track the on-going care that is being provided throughout their system, and join in real-time to provide guidance or advice.

Remote rescuer 412 may thus perceive patient value PV 421 from other device 480, for example by viewing it on a screen, and make determinations about patient 482. Remote rescuer 412 may look up and send previous patient treatment history or reference information, patient demographics and insurance information, and transmit communications with the caregivers via audio or text communication to affect the care of patient 482, document patient and event information associated with the care of patient 482 including, Emergency Crew information, and make transport decisions.

Communication module 490 can be further configured to receive from communication network 482 an incoming message 483. This reception is indicated in FIG. 4 with arrow 481. Incoming message 483 may or may not originate from other device 480.

Incoming message 483 may have been generated by remote rescuer 412 responsive to perceiving patient value PV 421 from other device 480. Incoming message 483 can contain an encoded sound SD 484, which can be one or more segments of the speech of remote rescuer 412. Speaker 471 can be configured to play sound SD 484 to local rescuer 411, after decoding it from incoming message 483. Sound SD 484 can be thus played with screen 472 displaying patient value PV 421. System 400 may also include a processor 430, which can be as processor 330, and which can be configured to decode sound SD 484 from incoming message 483, so that sound SD 484 can be played on speaker 471. This way, the segments of the speech can be played to construct the speech of remote rescuer 412 for guiding local rescuer 411. Local rescuer 411 may be assisted this way by remote rescuer 412, who may be better trained than local rescuer 411.

It will be appreciated that engaging remote rescuer 412 may not happen every time. For example, there are times when system 400 is not used to help a patient. There can be other times when patient 482 is being helped, but local rescuer 411 has not had the opportunity to engage remote rescuer 412, or forgets, perhaps under the stress of the moment.

In some embodiments, if the patient value exceeds a threshold, system 400 performs one or more additional functions automatically. The patient value, and the corresponding threshold, can be chosen according to possible conditions. For example, the patient value could be the patient's temperature, indicating a fever. Or it could be a slope at a certain portion of an ECG waveform, indicating an AMI. Or it could be an infinite impedance value, which could indicate that an electrode has fallen off.

In such embodiments, communication module 490 can be configured to thus transmit patient value PV 421 automatically. Or, screen 472 can be further configured to display a remote connect prompt to local rescuer 411. Or, speaker 471 can be further configured to play a remote connect prompt to local rescuer 411.

In some embodiments, a processor of system 400, such as processor 430, is configured to determine whether incoming message 483 was indeed received in response to patient value PV 421 that was transmitted according to arrow 491. In other words, the incoming message is authenticated first. In such embodiments, if it is not so determined, sound SD 484 is not played by speaker 471. A more particular example is now described.

Figure 5:
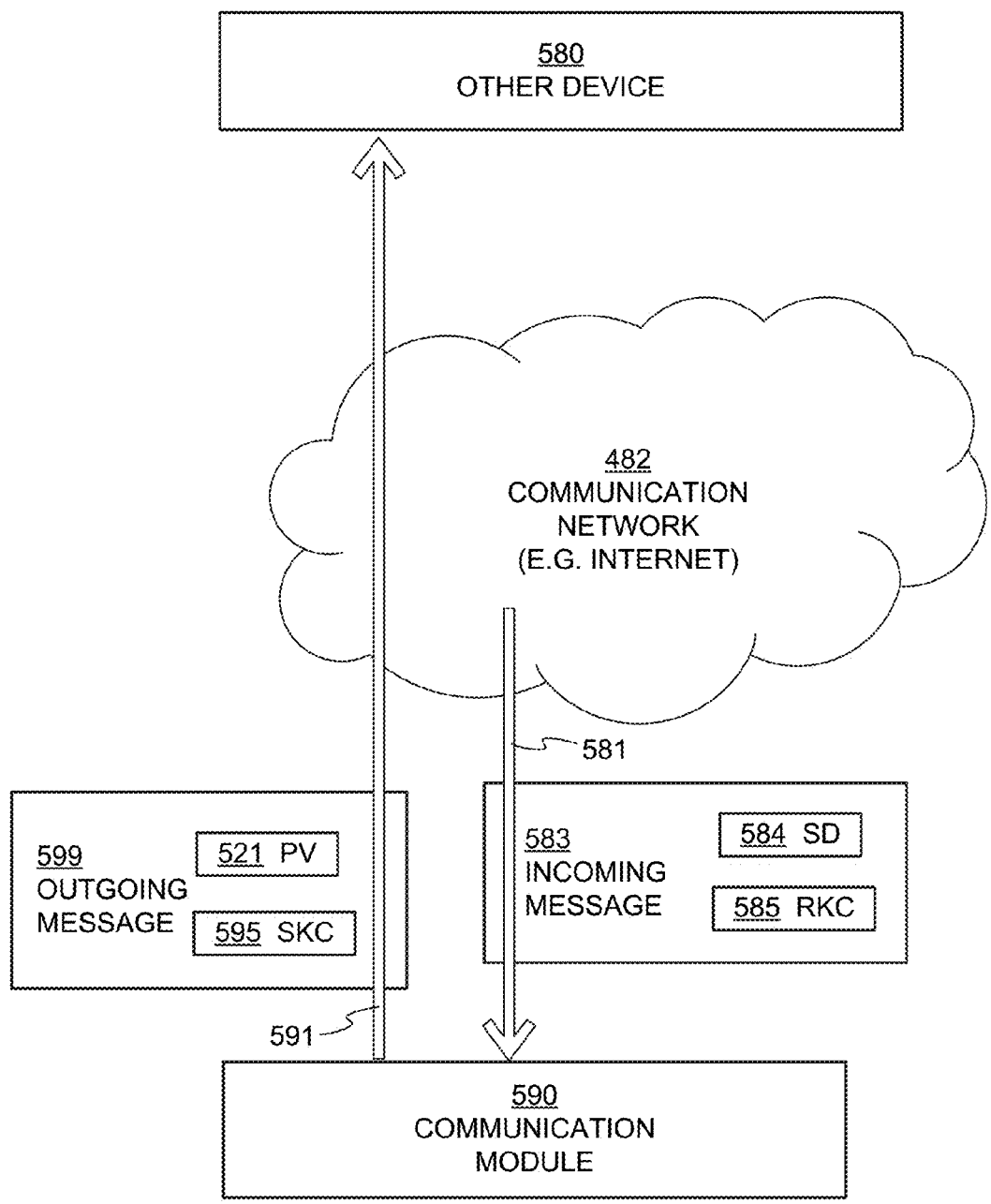
FIG. 5 is a diagram of a sample authentication scheme according to embodiments.

FIG. 5 is a diagram of a sample authentication scheme according to embodiments. A communication module 590, which can be as communication module 490, is configured to transmit an outgoing message 599 to another device 580. This transmission can be according to arrow 591, and it is via communication network 482. Other device 580 can be as other device 480. Outgoing message 599 contains a patient value PV 521, which can be as patient value PV 421. Of course, patient value PV 521 is in encoded form, for transmission via communication network 482. In addition, outgoing message 599 may contain a send key code SKC 595. Send key code SKC 595 can be generated in a number of ways, for example as a hash of patient value PV 521, from a time stamp, etc.

Communication module 590 is configured to further receive an incoming message 583 via communication network 482, as shown by arrow 581. Incoming message 583 contains an encoded sound SD 584, and the desire is to authenticate whether that sound SD 584 is indeed received in response to the transmitted patient value PV 521. Incoming message 583 also contains a return key code RKC 585. In such embodiments, the determination of whether incoming message 583 was indeed received in response to transmitted patient value PV 521 is performed by comparing return key code RKC 585 to send key code SKC 595.

In some embodiments, the incoming message further contains an encoded image, which can even be part of a stream of images. In such embodiments, an external defibrillator system can display the image, and even the stream of images, after decoding. Examples are now described.

Figure 6:
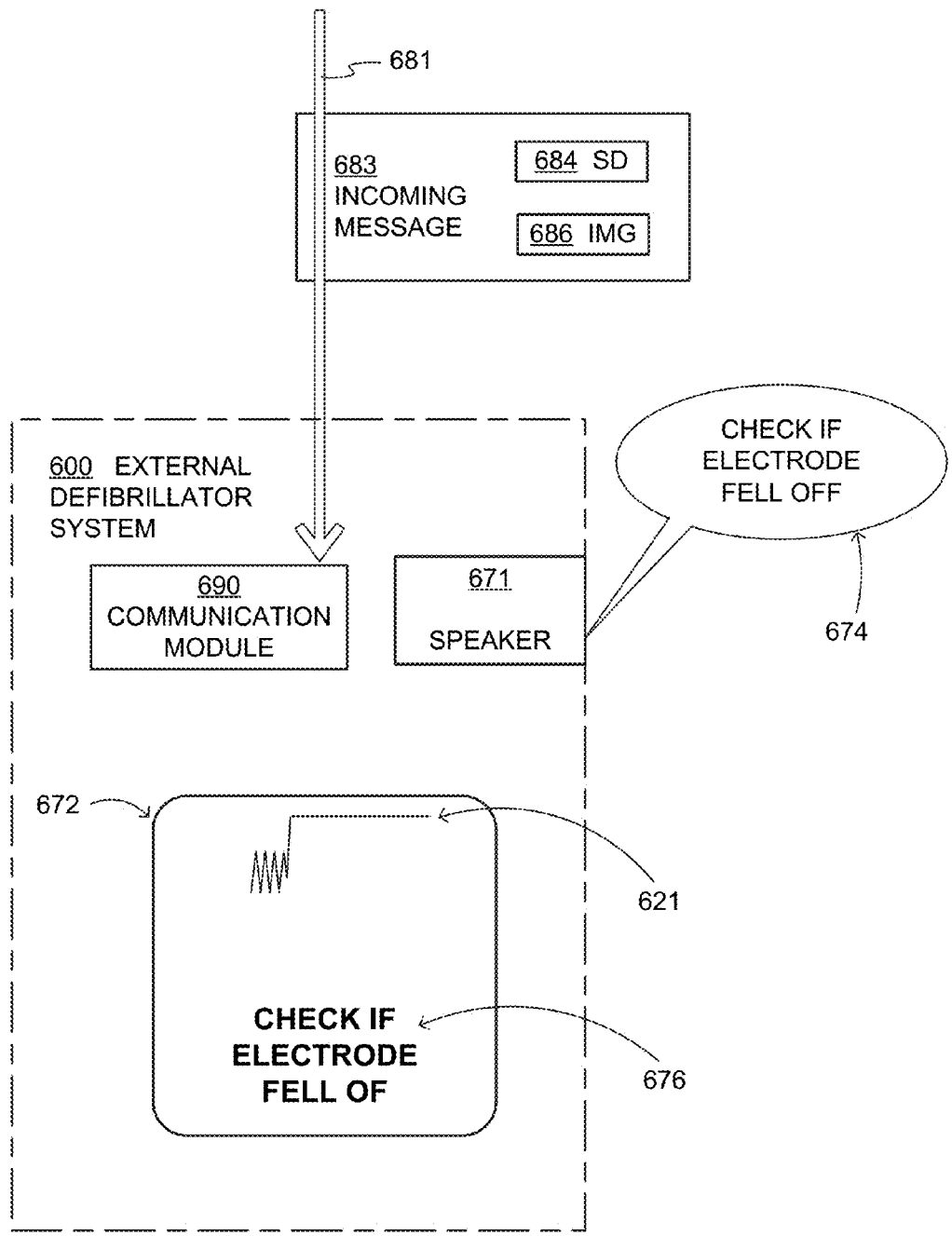
FIG. 6 is a diagram showing sample components of an external defibrillator system according to an embodiment where an incoming image is displayed concurrently with a sound being played.

FIG. 6 is a diagram showing sample components of an external defibrillator system 600 that has a communication module 690. System 600 includes a speaker 671 and a screen 672. A sensor (not shown) generates a patient value 621 that is shown on screen 672. In this example, patient value 621 is a waveform of impedance while the patient is receiving CPR chest compressions. It will be observed that initially the impedance oscillates consistently with the administration of CPR, and then it becomes a flat maximum value.

Communication module 690 receives an incoming message 683 according to an arrow 681. Incoming message 683 contains an encoded sound SD 684, which is played as a decoded sound 674 by speaker 671.

Incoming message 683 further contains an encoded image IMG 686. Screen 672 is further configured to display the decoded image 676, concurrently with displaying patient value 621.

Figure 7:
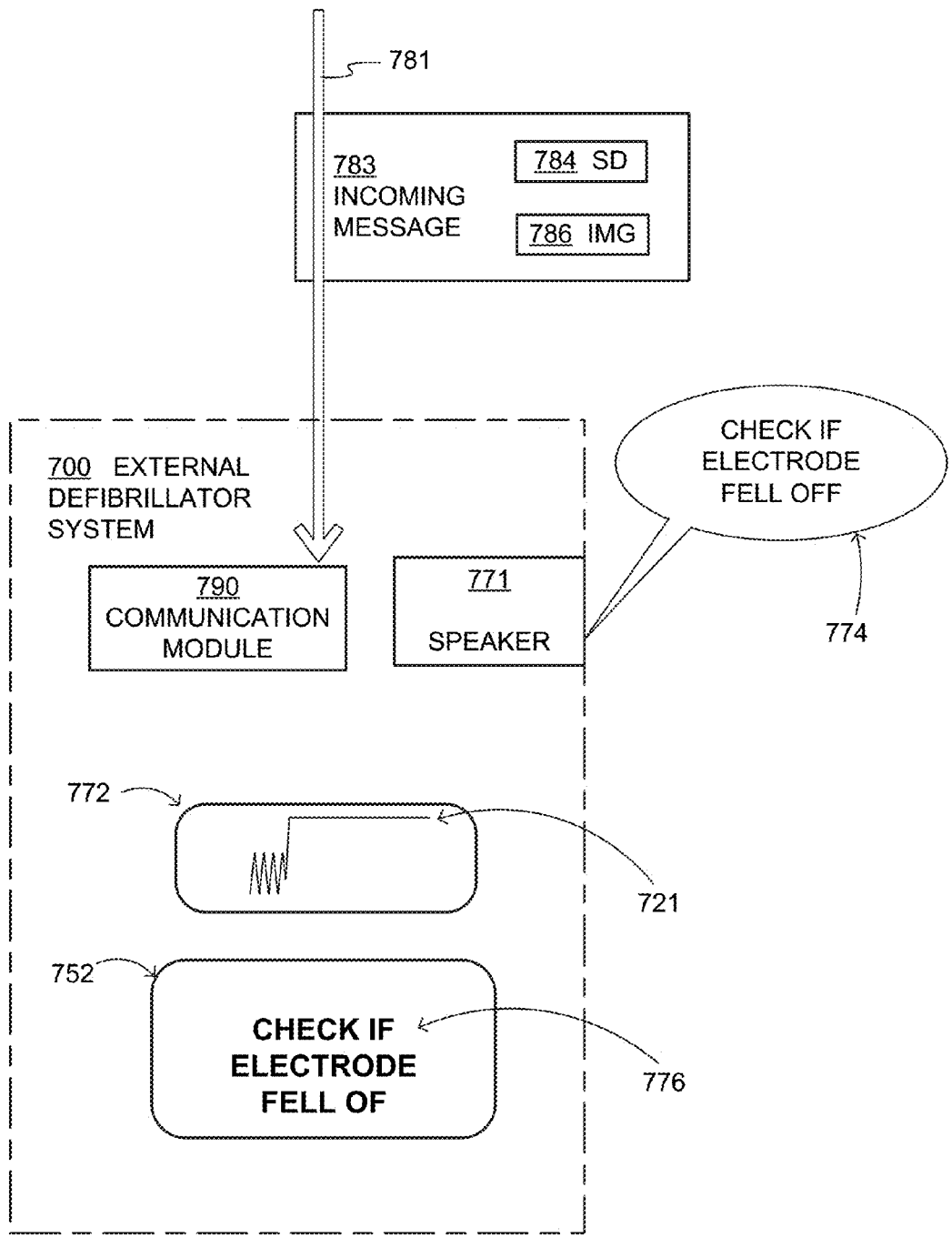
FIG. 7 is a diagram showing sample components of an external defibrillator system according to another embodiment where an incoming image is displayed concurrently with a sound being played.

FIG. 7 is a diagram showing sample components of an external defibrillator system 700 that has a communication module 790. System 700 includes a speaker 771, a screen 772, and another screen 752. A sensor (not shown) generates a patient value 721 that is shown on screen 772, and which is similar to patient value 621.

Communication module 790 receives an incoming message 783 according to an arrow 781. Incoming message 783 contains an encoded sound SD 784, which is played as a decoded sound 774 by speaker 771.

Incoming message 783 further contains an encoded image IMG 786. Screen 752 is configured to display the decoded image 776, concurrently with screen 772 displaying patient value 721.

The devices and/or systems mentioned in this document perform functions, processes and/or methods. These functions, processes and/or methods may be implemented by one or more devices that include logic circuitry. Such a device can be alternately called a computer, and so on. It may be a standalone device or computer, such as a general purpose computer, or part of a device that has one or more additional functions. The logic circuitry may include a processor that may be programmable for a general purpose, or dedicated, such as a microcontroller, a microprocessor, a Digital Signal Processor (DSP), etc. The logic circuitry may also include non-transitory computer-readable storage media, such as memories. Such media can be of different types including but not limited to volatile memory, non-volatile memory (NVM), read only memory (ROM); random access memory (RAM); magnetic disk storage media; optical storage media; smart cards, flash memory devices, etc. These storage media, individually or in combination with others, can have stored thereon data. In addition, these storage media may store programs that the processor may be able to read, and execute. More particularly, the programs can include instructions in the form of code, which the processor may be able to execute upon reading. Executing is performed by physical manipulations of physical quantities, and may result in the functions, processes, actions and/or methods to be performed, and/or the processor to cause other devices or components or blocks to perform such functions, processes, actions and/or methods. Often, for the sake of convenience only, it is preferred to implement and describe a program as various interconnected distinct software modules or features. These, along with data are individually and also collectively known as software. In some instances, software is combined with hardware, in a mix called firmware.

Moreover, methods and algorithms are described below. These methods and algorithms are not necessarily inherently associated with any particular logic device or other apparatus. Rather, they are advantageously implemented by programs for use by a computing machine, such as a general-purpose computer, a special purpose computer, a microprocessor, etc. These algorithms are not necessarily purely mathematical, and are configured to address challenges particular to the problem solved, as will be apparent to a person skilled in the art.

This detailed description includes flowcharts, display images, algorithms, and symbolic representations of program operations within at least one computer readable medium. An economy is achieved in that a single set of flowcharts is used to describe both programs, and also methods. So, while flowcharts describe methods in terms of boxes, they also concurrently describe programs.

Methods are now described.

Figure 8:
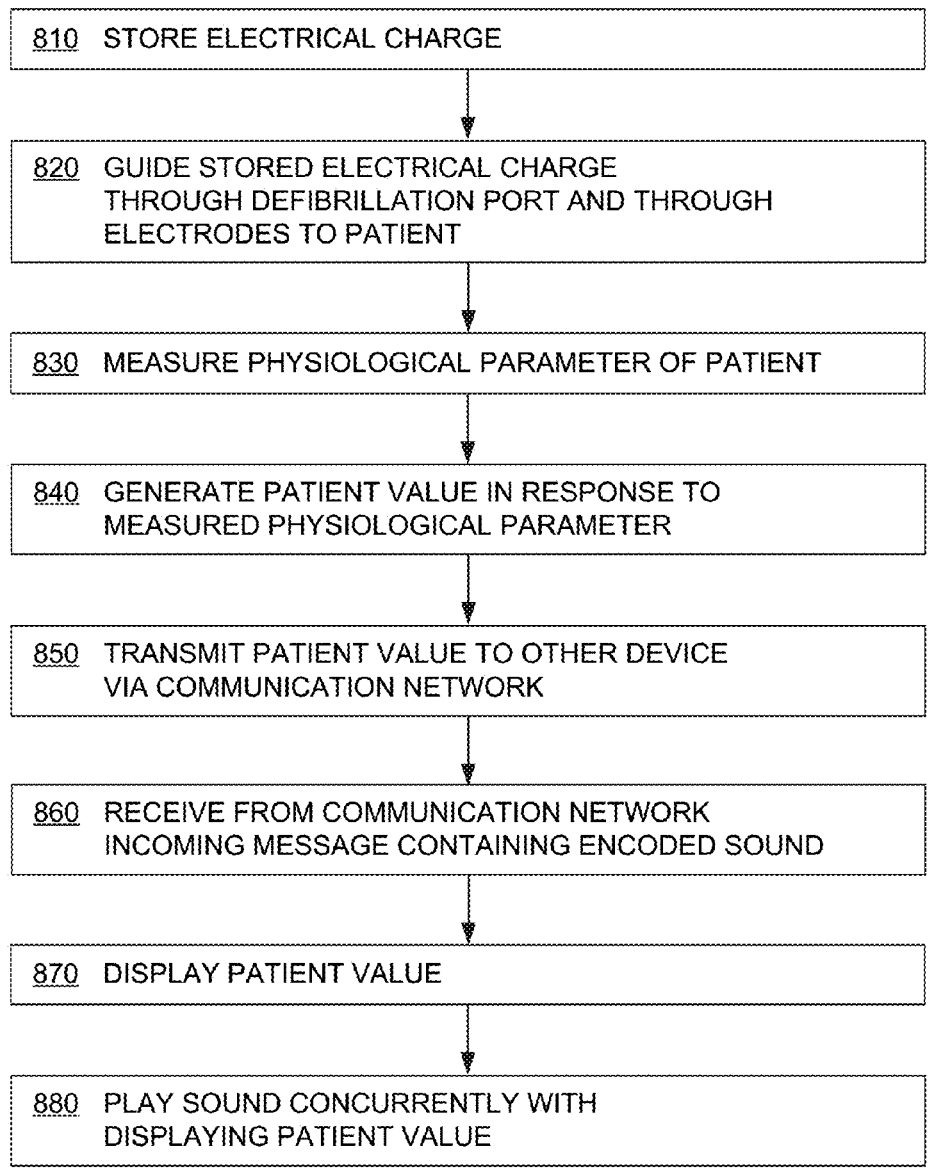
FIG. 8 is a flowchart for illustrating methods according to embodiments.

FIG. 8 shows a flowchart 800 for describing methods according to embodiments. According to an operation 810, an electrical charge is stored.

According to another operation 820, the stored electrical charge is guided through the defibrillation port and through electrodes to a patient.

According to another operation 830, a physiological parameter of the patient is measured. The physiological parameter can be the patient's ECG signal, impedance signal, peripheral capillary oxygen saturation, carboxyhemoglobin, methemoglobin, end-tidal carbon dioxide, non-invasive blood pressure, tissue oxygen saturation, temperature, a regional oxygen saturation index, and an invasive pressure.

According to one more operation 840, a patient value is generated in response to the measured physiological parameter.

According to another operation 850, the patient value is transmitted to another device via a communication network. The transmission can be initiated by a local rescuer, or performed routinely as part of the established communication with the other device of the remote rescuer. In some embodiments, the patient value is transmitted automatically if the patient value exceeds a threshold. Or, a remote connect prompt is issued to a local rescuer if this happens. The remote connect can be displayed as an image, played as a sound prompt, etc. Upon perceiving the remote connect prompt, a local rescuer may initiate the connection and operation 850.

According to another operation 860, an incoming message is received from the communication network. The incoming message contains an encoded sound. The sound may be decoded from the incoming message.

According to another operation 870, the patient value of operation 840 is displayed on a screen.

According to another operation 880, the sound is played concurrently with displaying the patient value on the screen. In embodiments, it is further determined whether the incoming message was received in response to the transmitted patient value. If it is not so determined, the sound is not output from the speaker. The determination may take place as described above.

In some embodiments, the incoming message further contains an encoded image. In such embodiments, the image can be further displayed.

Returning to FIG. 4, in some embodiments remote rescuer 412 can also activate the defibrillation system 400, so as to discharge the stored charge through the patient and thus deliver electrotherapy. The discharge can be for defibrillation, pacing, etc. In other embodiments, the remote activation can take place without some of the features or operations of system 400. Accordingly, remote activation is now described as if it were a separate capability, although the description below can be extended capabilities for system 400 according to embodiments.

Figure 9:
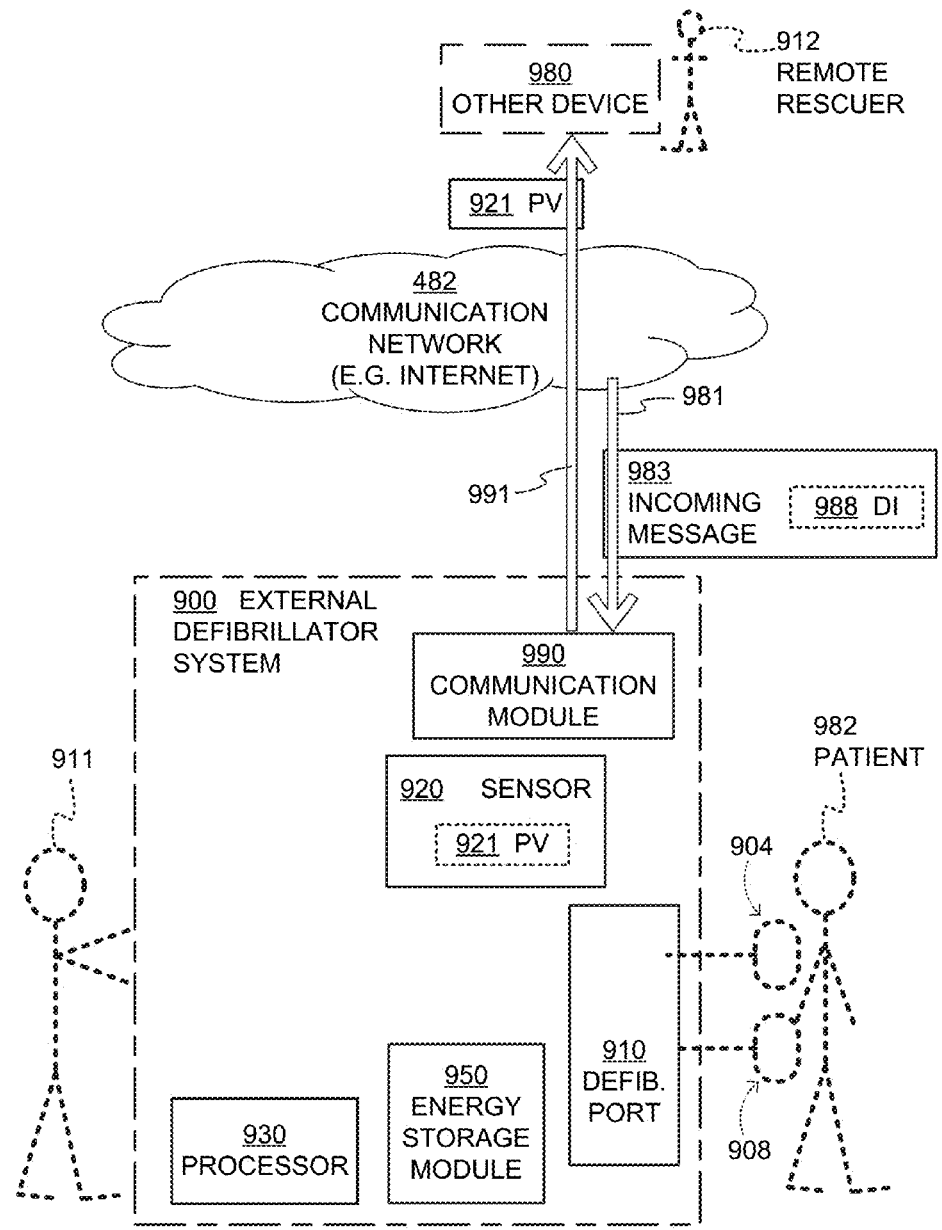
FIG. 9 is a diagram showing sample components of an external defibrillator system that is made and operates according to embodiments.

FIG. 9 is a diagram showing sample components of an external defibrillator system 900 that is made according to embodiments. External defibrillator system 900 can be a monitor-defibrillator that is used to respond to emergency patients in both the Hospital and Pre-Hospital Environments. System 900 is configured for use by a local rescuer 911 in cooperation with a remote rescuer 912 to assist a patient 982, similarly with what was described for FIG. 4. System 900 can assist patient 982 with the help of electrodes 904, 908, which can be applied by local rescuer 911.

Other features can also be as described in FIG. 4. For example, system 900 includes an energy storage module 950 that can be as energy storage module 350, a defibrillation port 910 that can be as defibrillation port 310, and a sensor 920 that can be as measurement circuit 320 or other sensor 325. Sensor 920 can be configured to measure a physiological parameter of patient 982, and to generate a patient value PV 921 in response to the measured physiological parameter, as described in more detail above. In addition, a user interface (not shown in FIG. 9) may be provided for local rescuer 911 to operate system 900, and also possibly to communicate with remote rescuer 912.

System 900 also includes a communication module 990, which can be as was described for communication module 390. Communication module 990 can be configured to transmit patient value PV 921 to another device 980 via a communication network 482. This transmission is indicated in FIG. 9 with arrow 991. Other device 980 can be as other device 480, and can be used by remote rescuer 912. Remote rescuer 912 may thus view patient value PV 921 on other device 980, and make determinations about patient 982.

Communication module 990 can be further configured to receive from communication network 482 an incoming message 983. This reception is indicated in FIG. 9 with arrow 981. Incoming message 983 may or may not originate from other device 980.

Incoming message 983 may have been generated by remote rescuer 912 responsive to perceiving patient value PV 921 from other device 980. Incoming message 983 can contain an encoded discharge instruction DI 988.

System 900 may also include a processor 930, which can be as processor 330. Processor 930 can be configured to decode discharge instruction DI 988 from incoming message 983. Processor 930 can be further configured to cause, responsive to the decoded discharge instruction, the electrical charge stored in module 950 to be guided via defibrillation port 910 and via electrodes 904, 908 to patient 982 for administering therapy.

This way, remote rescuer 912 can remotely activate defibrillator system 900 by transmitting discharge instruction DI 988. Remote rescuer 912 may have more confidence in performing this drastic action than local rescuer 911.

Other previously described features may also apply. For example, in some embodiments, if the patient value exceeds a threshold, system 900 performs one or more additional functions automatically. In such embodiments, communication module 990 could be configured to thus transmit patient value PV 921 automatically, and so on. Or, if an interface is included, a remote connect prompt can be issued to local rescuer 911.

For another example, in some embodiments, a processor of system 900, such as processor 930, is configured to determine whether incoming message 983 was indeed received in response to patient value PV 921 that was transmitted according to arrow 991. In other words, the incoming message is authenticated first. In such embodiments, if it is not so determined, the stored electrical charge is not so guided, and so on. Authentication may happen in a number of ways, for example as was described in FIG. 5.

FIG. 10 shows a flowchart 1000 for describing methods according to embodiments. Operations 1010, 1030, 1040 and 1050 are similar to operations 810, 830, 840 and 850 respectively.

According to another operation 1060, an incoming message is received from the communication network. The incoming message contains an encoded discharge instruction.

According to another operation 1070, the discharge instruction is decoded from the incoming message.

According to another operation 1090, responsive to the decoded discharge instruction, the stored electrical charge is caused to be guided via the defibrillation port and via the coupled electrodes to the patient. In some embodiments, it is further determined whether the incoming message was received in response to the transmitted patient value. If it is not so determined, then the stored electrical charge is not caused to be so guided. The determination may take place as described above.

In the methods described above, each operation can be performed as an affirmative step of doing, or causing to happen, what is written that can take place. Such doing or causing to happen can be by the whole system or device, or just one or more components of it. It will be recognized that the methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily this description. Plus, any reference to any prior art in this description is not, and should not be taken as, an acknowledgement or any form of suggestion that such prior art forms parts of the common general knowledge in any country or any art.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In this document, the phrases "constructed to" and/or "configured to" denote one or more actual states of construction and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Any and all parent, grandparent, great-grandparent, etc. patent applications, whether mentioned in this document or in an Application Data Sheet (ADS) of this patent application, are hereby incorporated by reference herein, including any priority claims made in those applications and any material incorporated by reference, to the extent such subject matter is not inconsistent herewith.

In this description a single reference numeral may be used consistently to denote a single aspect, component, or process. Moreover, a further effort may have been made in the drafting of this description to choose similar though not identical reference numerals to denote versions or embodiments of an aspect, component or process that are the same or possibly different. Where made, such a further effort was not required, but was nevertheless made gratuitously to accelerate comprehension by the reader. Even where made in this document, such an effort might not have been made completely consistently throughout the many versions or embodiments that are made possible by this description. Accordingly, the description controls. Any similarity in reference numerals may be used to confirm a similarity in the text, or even possibly a similarity where express text is absent, but not to confuse aspects where the text or the context indicates otherwise.

The claims of this document define certain combinations and subcombinations of elements, features and steps or operations, which are regarded as novel and non-obvious. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that it can have one or more of this component or item.

What is claimed is:

1. An external defibrillator system configured for use by a local rescuer in cooperation with a remote rescuer to assist a patient, the local rescuer capable of carrying the external defibrillator system and of attaching electrodes to the patient, the external defibrillator system comprising:
   an energy storage module configured to store an electrical charge;
   a defibrillation port configured such that the electrodes can be electrically coupled to the defibrillation port by the local rescuer;
   a sensor configured to measure a physiological parameter of the patient, and to generate a patient value in response to the measured physiological parameter;
   a communication module configured to transmit the patient value to another device via a communication network, the communication module further configured to receive from the communication network an incoming message, the incoming message generated by the remote rescuer responsive to perceiving the patient value from the other device, the incoming message containing an encoded discharge instruction;
   a processor configured to:

decode the discharge instruction from the incoming message, and cause, responsive to the decoded discharge instruction, the stored electrical charge to be guided via the defibrillation port and via the coupled electrodes to the patient.

2. The external defibrillator system of claim 1, in which the patient value is a value of an ECG signal or an impedance signal.

3. The external defibrillator system of claim 1, in which the physiological parameter is one of the patient's peripheral capillary oxygen saturation, carboxyhemoglobin, methemoglobin, end-tidal carbon dioxide, non-invasive blood pressure, tissue oxygen saturation, temperature, a regional oxygen saturation index, and an invasive pressure.

4. The external defibrillator system of claim 1, in which the communication module is configured to thus transmit the patient value automatically responsive to the patient value exceeding a threshold.

5. The external defibrillator system of claim 1, further comprising:
a processor configured to determine whether the incoming message was received in response to the transmitted patient value, and
if it is not so determined, the stored electrical charge is not so guided.

6. The external defibrillator system of claim 5, in which the communication module is configured to transmit an outgoing message to the other device,
the outgoing message contains the patient value in encoded form,
the outgoing message contains a send key code,
the incoming message contains a return key code, and
the determination is performed by comparing the return key code to the send key code.

7. The external defibrillator system of claim 6, in which the send key code is generated as a hash of the patient value.

8. A non-transitory computer-readable storage medium storing one or more programs, at least one of the one or more programs including a protocol, in which, when the one or more programs are executed by an external defibrillator system that includes a processor that is configured to operate according to the protocol, an energy storage module, a defibrillation port configured such that electrodes can be electrically coupled to the defibrillation port, a sensor, and a communication module, they result in operations comprising:
storing an electrical charge in the energy storage module;
measuring, by the sensor, a physiological parameter of the patient;
generating a patient value in response to the measured physiological parameter;
transmitting, by the communication module, the patient value to another device via a communication network;
receiving via the communication network an incoming message, the incoming message containing an encoded discharge instruction, the incoming message generated by a remote human rescuer responsive to the remote rescuer perceiving the patient value from the other device;
decoding the discharge instruction from the incoming message; and causing, responsive to the decoded discharge instruction, the stored electrical charge to be guided via the defibrillation port and via the coupled electrodes to the patient, but
in which the stored protocol does not become altered responsive to the incoming message.

9. The medium of claim 8, in which
the patient value is a value of an ECG signal or an impedance signal.

10. The medium of claim 8, in which
the physiological parameter is one of the patient's peripheral capillary oxygen saturation, carboxyhemoglobin, methemoglobin, end-tidal carbon dioxide, non-invasive blood pressure, tissue oxygen saturation, temperature, a regional oxygen saturation index, and an invasive pressure.

11. The medium of claim 8, in which
the patient value is transmitted automatically responsive to the patient value exceeding a threshold.

12. The medium of claim 8, in which when the one or more programs are so executed, they result in the operations to further comprise:
determining whether the incoming message was received in response to the transmitted patient value, and
in which if it is not so determined, the stored electrical charge is not caused to be so guided.

13. The medium of claim 12, in which
the communication module transmits an outgoing message to the other device,
the patient value is encoded in the outgoing message,
the outgoing message includes a send key code,
the incoming message includes a return key code, and
the determination is performed by comparing the return key code to the send key code.

14. The medium of claim 13, in which
the send key code is generated as a hash of the patient value.

15. A method for an external defibrillator system that includes an energy storage module, a defibrillation port configured such that electrodes can be electrically coupled to the defibrillation port, a sensor, and a communication module, the method comprising:
storing an electrical charge in the energy storage module;
measuring, by the sensor, a physiological parameter of the patient;
generating a patient value in response to the measured physiological parameter;
transmitting, by the communication module, the patient value to another device via a communication network;
receiving via the communication network an incoming message, the incoming message generated by a remote human rescuer responsive to the remote rescuer perceiving the patient value from the other device, the incoming message containing an encoded discharge instruction;
decoding the discharge instruction from the incoming message; and
causing, responsive to the decoded discharge instruction, the stored electrical charge to be guided via the defibrillation port and via the coupled electrodes to the patient.

16. The method of claim 15, in which
the patient value is a value of an ECG signal or an impedance signal.

17. The method of claim 15, in which
the physiological parameter is one of the patient's peripheral capillary oxygen saturation, carboxyhemoglobin, methemoglobin, end-tidal carbon dioxide, non-invasive blood pressure, tissue oxygen saturation, temperature, a regional oxygen saturation index, and an invasive pressure.

18. The method of claim 15, in which
the patient value is transmitted automatically responsive to the patient value exceeding a threshold.

19. The method of claim 15, further comprising:
determining whether the incoming message was received in response to the transmitted patient value, and
in which if it is not so determined, the stored electrical charge is not caused to be so guided.

20. The method of claim 19, in which
the communication module transmits an outgoing message to the other device,
the patient value is encoded in the outgoing message,
the outgoing message includes a send key code,
the incoming message includes a return key code, and
the determination is performed by comparing the return key code to the send key code.

21. The method of claim 20, in which
the send key code is generated as a hash of the patient value.

* * * * *

UNITED STATES PATENT AND TRADEMARK OFFICE
CERTIFICATE OF CORRECTION

PATENT NO.        : 9,707,408 B2                         Page 1 of 1
APPLICATION NO.   : 15/154897
DATED             : July 18, 2017
INVENTOR(S)       : Peterson et al.

It is certified that error appears in the above-identified patent and that said Letters Patent is hereby corrected as shown below:

In the Specification

In Column 4, Line 5, Delete "(SpO2)," and insert -- ($SpO_2$), --, therefor.

In Column 4, Line 8, Delete "(EtCO2)," and insert -- ($EtCO_2$), --, therefor.

In Column 4, Line 10, Delete "(StO2)," and insert -- ($StO_2$), --, therefor.

In Column 4, Line 11, Delete "(RsO2)," and insert -- ($RsO_2$), --, therefor.

In Column 4, Line 15, Delete "(SpO2)," and insert -- ($SpO_2$), --, therefor.

Signed and Sealed this
Twenty-eighth Day of November, 2017

Joseph Matal
*Performing the Functions and Duties of the*
*Under Secretary of Commerce for Intellectual Property and*
*Director of the United States Patent and Trademark Office*